Figure 1:
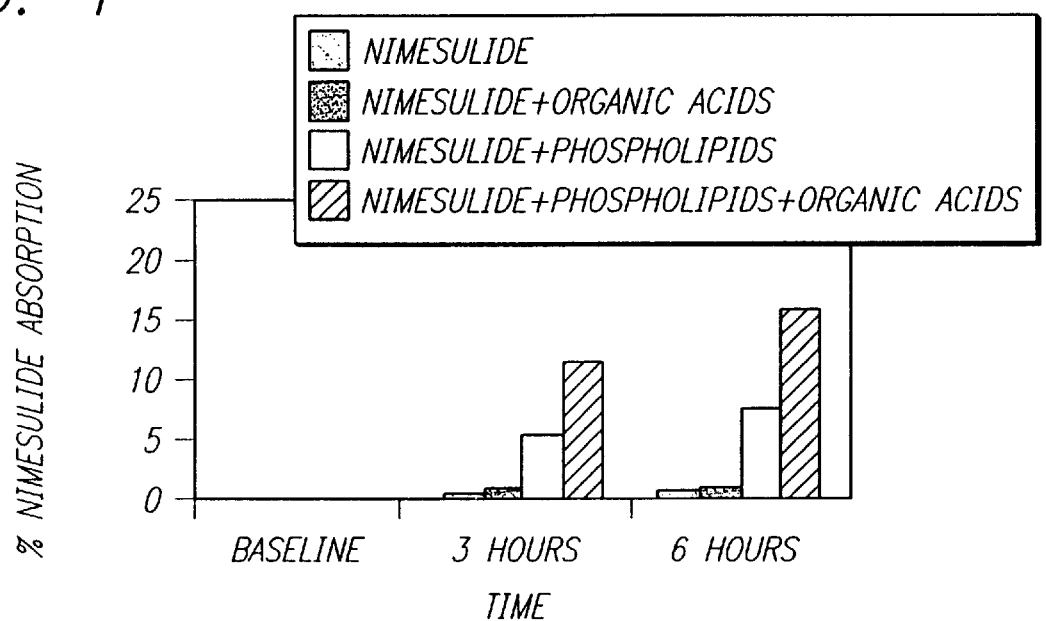

United States Patent [19]
Giorgetti

[11] Patent Number: 5,998,480
[45] Date of Patent: Dec. 7, 1999

[54] PHARMACEUTICAL PREPARATION CONTAINING NIMESULIDE FOR TOPICAL USE

[75] Inventor: Paolo Luca Maria Giorgetti, Milan, Italy

[73] Assignee: Errekappa Eurotherapici S.P.A., Milan, Italy

[21] Appl. No.: 09/029,456

[22] PCT Filed: Jul. 2, 1997

[86] PCT No.: PCT/IB97/00816

§ 371 Date: May 4, 1998

§ 102(e) Date: May 4, 1998

[87] PCT Pub. No.: WO98/01124

PCT Pub. Date: Jan. 15, 1998

[30] Foreign Application Priority Data

Jul. 5, 1996 [IT] Italy ................................ RM96A0480

[51] Int. Cl.$^6$ .................................................. A61K 31/63
[52] U.S. Cl. ............................................................ 514/604
[58] Field of Search ............................................. 514/604

[56] References Cited

U.S. PATENT DOCUMENTS

| | | | |
|---|---|---|---|
| 5,654,337 | 8/1997 | Roentsch et al. | 514/570 |
| 5,716,609 | 2/1998 | Jain et al. | 424/78.05 |
| 5,763,422 | 6/1998 | Lichtenberger et al. | 514/78 |
| 5,814,659 | 9/1998 | Elden | 514/452 |
| 5,830,499 | 11/1998 | Bouwstra | 424/450 |
| 5,837,289 | 11/1998 | Grasela et al. | 424/484 |

FOREIGN PATENT DOCUMENTS

| | | |
|---|---|---|
| 801812 | 1/1974 | Belgium . |
| 0 367 382A | 5/1990 | European Pat. Off. . |
| 0532900 | 3/1993 | European Pat. Off. . |
| 0 843 998A | 5/1998 | European Pat. Off. . |
| 2662360 | 11/1991 | France . |
| 4116659 | 11/1991 | Germany . |
| 299 500 | 2/1997 | New Zealand . |
| PCT/IT91/ 00043 | 11/1991 | WIPO . |
| PCT/HU94/ 00014 | 12/1994 | WIPO . |
| WO 96/11002 | 4/1996 | WIPO . |

OTHER PUBLICATIONS

Int. J. Tiss. Reac., vol. 15, No. 6, 1993, pp. 225–234, XP002048767 M. Facino: "Antioxidant Profile of Nimesulide, Indomethacin and Diclofenac in Phosphatidylcholine Liposomes (PCL) as Membrane Model".

Drug Invest., vol. 3, No. suppl. 2, 1991, pp. 10–13, XP002048768 G.P. Velo: "The Antiinflammatory, Analgesic and Antipyretic Activity of Nimesulide in Experimental Models."

Acta Toxicol. Ther., vol. 10, No. 2, 1989, pp. 169–177, XP002048769 M. Tortorici: "Terapia Delle Ottiti Esterne Con La Nimesulide".

Eur. J. Dermatol., vol. 4, No. 4, 1994, pp. 337–338, XP002048770 S. Veraldi: "Treatment of Erosive Pustular Dermatosis of the Scalp with Nimesulide".

Dialog Select, The Merick Index Online, CAS Registry No. 51803–78–2 for nimesulide, Dialog File No. 304, Accession No. 006640 (1997).

Analytical Abstracts, Dialog File No. 305, Accession No. 273305 (1997), Abstract for Alvarez–Lueje, A., et al., "Voltammetric Study of Nimesulide and Its Differential Pulse Polarographic Determination in Pharmaceuticals", *Electroanalysis*, 9(15), pp. 1209–1213, (New York, Oct. 1997).

Analytical Abstracts, Dialog File No. 305, Accession No. 269327 (1997), Abstract for Chowdary, K.P.R., et al., "A New Spectrophotometric Method for the Determination of Nimesulide", *Indian Drugs*, 34(7), pp. 396–398, (Jul. 1997).

Analytical Abstracts, Dialog File No. 305, Accession No. 263471 (1997), Abstract for Sarkar, P., et al., "A Unique Metabolite of Nimesulide", *J. Anal. Toxicol.*, 21(3), pp. 197–202 (May–Jun. 1997).

Susan Buvadari, et al., eds., *The Merck Index*; (Rahway, New Jersey: Merck & Co., Inc., 1989), 1035.

Munhoz, M., et al. "Estudo Comparativo Entre Nimesulide Versus Diclofenaco Potassico Em Afeccoes Otorrinolaringologicas: Comparative Study with Nimesulide vs. Potassium Diclofenac in ENT Disease," Revista Da Sociedada Brasileria de Medicina Tropical, vol. 47, No. 11, Nov. 1990, pp. 591–594, XP000563507.

*Primary Examiner*—James H. Reamer
*Attorney, Agent, or Firm*—Ladas & Parry

[57] ABSTRACT

The subject matter of this invention is a pharmaceutical preparation for topical use containing as active principle nimesulide (CAS No. 51 803-78-2) or one of its active derivatives. The invention is characterized by the fact that the preparation's base contains at least one phospholipid and at least one substance with acid reaction, specifically an acid. The figure reports the results of an ex vivo nimesulide absorption test performed with topical formulations including those which are the subject matter of this invention.

33 Claims, 1 Drawing Sheet

PHARMACEUTICAL PREPARATION CONTAINING NIMESULIDE FOR TOPICAL USE

The subject matter of this invention are topical preparations based on nimesulide containing phospholipids and organic or inorganic acids.

As is known, nimesulide(4-nitro-2-phenoxy-methansulfanilide) is a nonsteroidal anti-inflammatory drug, that has been well-known for some time, with analgesic and antipyretic activity (BE 801812). This molecule is used in the treatment of articular and extra-articular inflammatory conditions with pain related to rheumatoid arthritis, as well as cataract (EP 0 532900 A). Nimesulide has demonstrated as having a better therapeutical ratio, less gastrolesivity and, in general, better tolerability with respect to other nonsteroidal anti-inflammatories such as for example, arylalkaloid acids such as acetylsalicylic acid, Ketoprofen, Diclofenac, Naproxen, thanks to the presence of a sulfanilide group in its molecule. Nimesulide appears to be very sparingly soluble in water (about 0.01 mg/ml at room temperature). Nimesulide's scarce water solubility and "wettability" can cause problems with drug release and constant bioavailability in various pharmaceutical forms.

In order to overcome such disadvantages, caused by nimesulide's low and variable bioavailability due to its scarce absorption properties (correlated with the very low solubility and bad "wetting" properties), it is possible to employ differing techniques.

Since nimesulide, a weak acid from the chemical viewpoint, is scarcely absorbed at low pH values (for example in the gastric tract), a possible initial step is salification with alkaline or alkaline-earth bases. This technique is not usually adopted, however, due to the very high pH of the salt solutions obtained.

A further method of increasing and achieving constant nimesulide bioavailability is complexation with cyclodextrins, above all β-cyclodextrins (as described in PCT/IT91/00043, DE 4116659 and PCT/HU94/00014) which enables better solubility and quicker absorption.

Another method, whose widest field of application is topical administration, is to vehicle the compound by using liposomal systems consisting of phospholipids.

In this specific sector there is, therefore, a demand for preparations based on nimesulide with better active principle bioavailability and absorption in the form of pharmaceutical presentations for topical application.

This invention is able to satisfy such requirement by also providing other advantages that will become evident further on.

The subject matter of this invention is a pharmaceutical preparation containing as active ingredient nimesulide (CAS-No. 51 803-78-2) or one of its active derivatives, characterized by the fact that the base of the preparation contains at least one phospholipid and at least one substance with an acid reaction, specifically an acid.

In the preparation according to this invention, nimesulide can be present at concentrations from 0.1 to 15%, the phospholipid from 0.1 to 10% and the acid from 0.1 to 10% of the preparation's weight.

In the preparation according to this invention, nimesulide can be present in dispersed form, the phospholipid can be a phosphatidyl acid ester, phosphatidylcholine in particular, and the acid can be an organic or an inorganic acid, preferably chosen from the group that comprises lactic acid, salicylic acid, glycolic acid, citric acid, aqueous hydrochloric acid.

The pH of the preparation according to this invention can preferably be between 1 and 7.

The preparation according to this invention can contain other substances acceptable by pharmaceutical carriers.

The preparation according to this invention can be in the form of a gel, lipogel, cream, ointment, lotion, foam, with and without propellants or pressurized gas. This invention is not limited to the pharmaceutical preparation containing nimesulide as active ingredient according to the preceding description. It is instead extended also to the use of the above mentioned preparation for formulation of drugs for topical use in the treatment of painful articular and extra-articular inflammation, rheumatoid arthritis, inflammation of soft tissues, whether accompanied by pain or not, and for the treatment of psoriasis and cataract.

The only figure attached shows—in an ex vivo test using a model that involves the use of Franz cells—the active ingredient concentration in the collection medium, at the beginning of the test, after 3 hours and after 6 hours, assayed by calculating the percentage of nimesulide which passes through the membrane that separates the donor compartment from the receptor compartment.

The manufacture of the pharmaceutical preparations according to this invention was carried out with techniques, apparatus and excipients that are traditionally used on a routine basis in the pharmaceutical industry such as, for example, those described in "Remington's Pharmaceutical Science Handbook", Mack Pub. Co., N.Y., U.S.A.

In vitro and ex vivo tests have been performed using the model that involves the use of Franz cells consisting of two compartments, a donor and a receptor, separated by an artificial or natural membrane on which a thin layer of test product is distributed. Rat skin was used as membrane for the tests, whilst pH 8 phosphate buffer solution was used as medium in the receptor compartment. The active principle concentration in the collection medium was assayed, using suitable techniques (HPLC), at the beginning of the test, after 3 and after 6 hours, with determination of the percentage of nimesulide which passed through the membrane.

The following formulations were used for the test:

| INGREDIENT | NIMESULIDE | NIMESULIDE + ORGANIC ACIDS | NIMESULIDE + PHOSPHOLIPIDS | NIMESULIDE + PHOSPHOLIPIDS + ORGANIC ACIDS |
|---|---|---|---|---|
| Nimesulide | 5.0% | 5.0% | 5.0% | 5.0% |
| Phosphatidylcholine | — | — | 3.0% | 3.0% |
| Polyacrylammide-Isoparaffin Laureth-7 | 4.0% | 4.0% | 4.0% | 4.0% |
| Methyl-p-hydroxybenzoate | 0.15% | 0.15% | 0.15% | 0.15% |
| Propyl-p-hydroxybenzoate | 0.05% | 0.05% | 0.05% | 0.05% |
| Lactic acid | — | 3.0% | — | 3.0% |
| Purified water (q.s. to) | 100% | 100% | 100% | 100% |

The results of an ex vivo test are reported in the figure.

From the in vitro and ex vivo tests it was noted that there is a correlation between percentage of phospholipids present and the quantity of drug that penetrates through the skin layers. Such drug quantity increased significantly by using organic acids (above all lactic acid and glycol acid) with keratolytic activity. Nimesulide's increased penetrating action, however, cannot be attributed to the sole presence of organic acids which, in the absence of phospholipids, do not influence nimesulide absorption. The possible keratolytic activity of the organic acids is not, therefore, the primary cause of the increased absorption, but, through synergetic activity with phospholipids, it contributes towards increasing availability of a drug, such as nimesulide, that has very scarce solubility.

The following examples represent methods of achieving a pharmaceutical preparation according to this invention:

EXAMPLE 1
Nimesulide gel—5% concentration

| | |
|---|---|
| Nimesulide | 5.0% |
| Phosphatidylcholine | 3.0% |
| Carboxyvinylpolymer (Carbopol 940) | 2.0% |
| Methyl-p-hydroxybenzoate | 0.17% |
| Propyl-p-hydroxybenzoate | 0.03% |
| Lactic acid | 5.0% |
| Purified water (q.s. to:) | 100% |

EXAMPLE 2
Nimesulide gel—5% concentration

| | |
|---|---|
| Nimesulide | 5.0% |
| Phosphatidylcholine | 3.0% |
| Polyacrylammide Isoparaffin Laureth-7 | 4.0% |
| Methyl-p-hydroxybenzoate | 0.15% |
| Propyl-p-hydroxybenzoate | 0.05% |
| Lactic acid | 3.0% |
| Purified water (q.s. to:) | 100% |

EXAMPLE 3
Nimesulide cream—3% concentration

| | |
|---|---|
| Nimesulide | 3.0% |
| Phosphatidylcholine | 1.0% |
| Glycerylmonostearate self-emulsion (Arlacel 165) | 7.0% |
| Methyl-p-hydroxybenzoate | 0.15% |
| Propyl-p-hydroxybenzoate | 0.05% |
| Citric acid monohydrate | 3.0% |
| Purified water (q.s. to:) | 100% |

I claim:

1. A pharmaceutical preparation comprising nimesulide as an active ingredient, a phospholipid, and at least one acid.

2. A pharmaceutical preparation according to claim 1, in which nimesulide is present at a concentration from 0.1 to 15% by weight of the preparation, the phospholipid is present at a concentration from 0.1 to 10% by weight of the preparation, and the acid is present at a concentration from 0.1 to 10% by weight of the preparation.

3. A pharmaceutical preparation according to claim 1, in which the nimesulide is present in dispersed form, the phospholipid is a phosphatidyl acid ester, and the acid is an organic or inorganic acid selected from the group consisting of lactic acid, salicylic acid, glycolic acid, citric acid, and aqueous hydrochloric acid.

4. A pharmaceutical preparation according to claim 2, wherein the pharmaceutical preparation has a pH between 1 and 7.

5. A pharmaceutical preparation according to claim 1, further comprising a substance acceptable for a pharmaceutical carrier.

6. A pharmaceutical preparation according to claim 1, wherein the pharmaceutical preparation is a gel, a lipogel, a cream, an ointment, a lotion, or a foam, with and without propellants or pressurized gas.

7. Utilization of a pharmaceutical preparation according to claim 1 to formulate a drug for topical use in treating painful articular and extra-articular inflammation, rheumatoid arthritis, inflammation of soft tissues with or without pain, psoriasis, or a cataract.

8. A pharmaceutical preparation as claimed in claim 1, wherein the acid is a substance with an acid reaction.

9. A pharmaceutical preparation as claimed in claim 3, wherein the phospholipid comprises phosphatidylcholine.

10. A pharmaceutical preparation as claimed in claim 2, wherein the pharmaceutical preparation further comprises a pharmaceutically acceptable carrier.

11. A pharmaceutical preparation as claimed in claim 2, wherein the phospholipid comprises a phosphatidyl acid ester.

12. A pharmaceutical preparation as claimed in claim 2, wherein the acid is selected from the group consisting of lactic acid, salicylic acid, glycolic acid, citric acid, and hydrochloric acid.

13. A pharmaceutical preparation as claimed in claim 12, wherein the phospholipid comprises phosphatidylcholine.

14. A pharmaceutical preparation as claimed in claim 10, wherein the phospholipid comprises a phosphatidyl acid ester.

15. A pharmaceutical preparation as claimed in claim 10, wherein the acid is selected from the group consisting of lactic acid, salicylic acid, glycolic acid, citric acid, and hydrochloric acid.

16. A pharmaceutical preparation as claimed in claim 15, wherein the phospholipid comprises phosphatidylcholine.

17. A pharmaceutical preparation as claimed in claim 2, wherein the pharmaceutical preparation has a pH between 1 and 7.

18. A pharmaceutical preparation as claimed in claim 3, wherein the pharmaceutical preparation has a pH between 1 and 7.

19. A pharmaceutical preparation as claimed in claim 10, wherein the pharmaceutical preparation has a pH between 1 and 7.

20. A pharmaceutical preparation as claimed in claim 13, wherein the pharmaceutical preparation has a pH between 1 and 7.

21. A pharmaceutical preparation as claimed in claim 16, wherein the pharmaceutical preparation has a pH between 1 and 7.

22. A pharmaceutical preparation as claimed in claim 1 for treating inflammation, rheumatoid arthritis, psoriasis, or a cataract.

23. A pharmaceutical preparation as claimed in claim 2 for treating inflammation, rheumatoid arthritis, psoriasis, or a cataract.

24. A pharmaceutical preparation as claimed in claim 3 for treating inflammation, rheumatoid arthritis, psoriasis, or a cataract.

25. A pharmaceutical preparation as claimed in claim 13 for treating inflammation, rheumatoid arthritis, psoriasis, or a cataract.

26. A pharmaceutical preparation as claimed in claim 16 for treating inflammation, rheumatoid arthritis, psoriasis, or a cataract.

27. A method of treating inflammation, rheumatoid arthritis, psoriasis, or a cataract, the method comprising topically utilizing a pharmaceutical preparation as claimed in claim 1.

28. A method of treating inflammation, rheumatoid arthritis, psoriasis, or a cataract, the method comprising topically utilizing a pharmaceutical preparation as claimed in claim 2.

29. A method of treating inflammation, rheumatoid arthritis, psoriasis, or a cataract, the method comprising topically utilizing a pharmaceutical preparation as claimed in claim 3.

30. A method of treating inflammation, rheumatoid arthritis, psoriasis, or a cataract, the method comprising topically utilizing a pharmaceutical preparation as claimed in claim 10.

31. A method of treating inflammation, rheumatoid arthritis, psoriasis, or a cataract, the method comprising topically utilizing a pharmaceutical preparation as claimed in claim 13.

32. A method of treating inflammation, rheumatoid arthritis, psoriasis, or a cataract, the method comprising topically utilizing a pharmaceutical preparation as claimed in claim 16.

33. A pharmaceutical preparation as claimed in claim 2, wherein the pharmaceutical preparation further comprises water.

* * * * *